US00PP24325P2

(12) United States Plant Patent

Klemm et al.

(10) Patent No.: US PP24,325 P2

(45) Date of Patent: Mar. 18, 2014

(54) *OSTEOSPERMUM* PLANT NAMED 'KLEOE12201'

(50) Latin Name: *Osteospermum ecklonis* Norl.
Varietal Denomination: KLEOE12201

(75) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/573,286

(22) Filed: Sep. 7, 2012

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct *Osteospermum* variety named 'KLEOE12201' particularly distinguished by light green foliage, good branching, and compact growth habit, is disclosed.

1 Drawing Sheet

Genus and species: *Osteospermum ecklonis* Norl.
Variety denomination: 'KLEOE12201'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE12201'. The new variety originated from a controlled cross conducted in July 2008 in Nairobi, Kenya between female *Osteospermum* plant named '07 183' (unpatented), and male *Osteospermum* plant named 'KLEO04113' (EU CPVR No. 21047). A single plant selection was subsequently chosen for further evaluation and asexual propagation.

The new variety was first propagated via vegetative cuttings in the spring of 2009 in Stuttgart, Germany. and has been asexually reproduced repeatedly by vegetative cuttings for three to four generations. The present invention has been found to retain its distinctive characteristics through successive asexual propagations via vegetative cuttings.

Plant Breeder's Rights for this variety have not been applied for. 'KLEOE12201' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Light green foliage;
2. Good branching; and
3. Compact growth habit.

DESCRIPTION OF THE PHOTOGRAPH

This new *Osteospermum* plant is illustrated by the accompanying photograph which shows overall plant habit including blooms, buds, and foliage of the plant in full color. The colors shown are as true as can be reasonably obtained by conventional photographic procedures. The photograph was taken in the spring of 2012 on a 3-month old plant grown in a heated glass greenhouse in Stuttgart, Germany, under conditions which approximate those generally used in normal horticultural practice.

DESCRIPTION OF THE NEW VARIETY

The following detailed descriptions set forth the distinctive characteristics of 'KLEOE12201'. The data which define these characteristics were collected from asexual reproductions carried out in Stuttgart, Germany. The plant history was taken in the spring of 2012 on 5-month old plants grown in 12 centimeter pots. The plants were grown in a heated glass greenhouse and pinched at week 32. Color readings were taken under natural and artificial light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Asteraceae.
- *Botanical name*.—*Osteospermum ecklonis* Norl.
- *Common name*.—African daisy.
- *Denomination*.—'KLEOE12201'.

Parentage:
- *Female parent*.—*Osteospermum* plant named '07 183' (unpatented).
- *Male parent*.—*Osteospermum* plant named 'KLEO04113' (EU CPVR No. 21047).

Plant:
- *Form and habit*.—Herbaceous perennial, usually cultivated as an annual.
- *Growth habit*.—Vigorous.
- *Branching habit*.—Freely branching.
- *Height (from top of soil)*.—17.0 cm.
- *Width (including inflorescence)*.—28.0 cm.
- *Propagation*.—Vegetative cuttings from tips.

*Time to produce a finished flowering plant.*—13 to 16 weeks.
*Time to initiate and develop roots.*—2 to 4 weeks.
*Root description.*—Freely rooting.

Leaves:
*Arrangement.*—Arranged in a whorl.
*Shape.*—Lanceolate.
*Apex.*—Acute.
*Base.*—Acute.
*Margin.*—Serrate.
*Color* (*both immature and mature leaves*).—Upper surface: RHS 141A. Lower surface: RHS 138A.
*Length.*—7.0 cm.
*Width.*—3.0 cm.
*Texture.*—Leathery.
*Petiole.*—Absent.

Stems:
*Total number of branches.*—15.
*Length.*—13.0 cm.
*Diameter.*—0.5 cm.
*Internode length.*—1.0 cm.
*Color.*—RHS 141D.
*Texture.*—Smooth.

Inflorescence buds:
*Shape.*—Obovate.
*Length.*—1.2 cm.
*Diameter.*—0.7 cm.
*Color* (*at tight bud just before the ray florets unfold*).—RHS 137C.

Inflorescence:
*Type.*—Single.
*Blooming habit.*—Spring to autumn.
*Quantity of inflorescences per plant.*—40.
*Lastingness of the inflorescences on the plant.*—12 days.
*Fragrance.*—Absent.
*Inflorescence diameter.*—6.0 cm.
*Disc diameter.*—1.1 cm.

Disc florets:
*Quantity per inflorescence.*—80.
*Shape.*—Oblanceolate.
*Tube color.*—Closed: RHS N79B. Mature: RHS N79C.
*Length.*—0.8 cm.
*Diameter* (*at apex*).—0.2 cm.
*Apex.*—Obtuse.
*Apex color.*—RHS N79B.
*Base.*—Fused to form a tube.
*Margin.*—Entire.

Ray florets:
*Quantity per inflorescence.*—16.
*Shape.*—Oblanceolate.
*Color.*—Upper surface: RHS N79B. Lower surface: RHS N77B.
*Length.*—3.0 cm.
*Width.*—0.9 cm.
*Apex.*—Obtuse.
*Base.*—Acute.
*Margin.*—Entire.
*Texture.*—Smooth.

Peduncle:
*Length.*—5.0 cm.
*Diameter.*—0.15 cm.
*Texture.*—Rough.
*Color.*—RHS 138A.

Phyllaries:
*Arrangement.*—Single.
*Observed quantity per inflorescence.*—22.
*Shape.*—Lanceolate.
*Color.*—Upper surface: RHS 138A. Lower surface: RHS 138B.
*Length.*—1.1 cm.
*Width.*—0.15 cm.
*Apex.*—Acute.
*Base.*—Obtuse.
*Margin.*—Entire.
*Texture.*—Rough.

Reproductive organs:
*Androecium.*—Location: Base of the disc floret corolla. Stamens: Quantity: 80. Shape: Filamentous. Color: RHS N77A. Filament length: 0.7 cm. Filament diameter: 0.05 cm. Anther: Shape: Elliptical. Color: RHS 200A. Length: 0.3 cm. Diameter: 0.09 cm. Pollen: Color: RHS 13A. Amount: Abundant.
*Gynoecium.*—Location: Base of the ray florets; stigmas in disc florets are degenerated and non-functional. Pistils: Number: 16. Length: 0.8 cm. Diameter: 0.03 cm. Stigma: Color: RHS N79A. Shape: Bipartite. Length: 0.2 cm. Diameter: 0.04 cm. Style: Color: RHS 79C. Length: 0.3 cm. Diameter: 0.03 cm. Shape: Filamentous.

Fruit and seed set: None observed.

Disease and insect/pest resistance: No specific observations were made.

COMPARISON WITH PARENTAL AND COMMERCIAL VARIETIES

'KLEOE12201' differs from the female parent *Osteospermum* plant '07 183' (unpatented) in that 'KLEOE12201' has good branching, whereas '07 183' has average branching.

'KLEOE12201' differs from the male parent *Osteospermum* plant 'KLEO04113' (EU CPVR No. 21047) in that 'KLEOE12201' has a compact growth habit and very good basal branching, whereas 'KLEO04113' has an upright growth habit and minimal branching.

'KLEOE12201' differs from the commercial *Osteospermum* plant 'KLEO04110' (U.S. Plant Pat. No. 18,272) in that 'KLEOE12201' has purple flowers, whereas 'KLEO04110' has violet purple flowers.

We claim:

1. A new and distinct variety of Osteospermum plant named 'KLEOE12201' as shown and described herein.

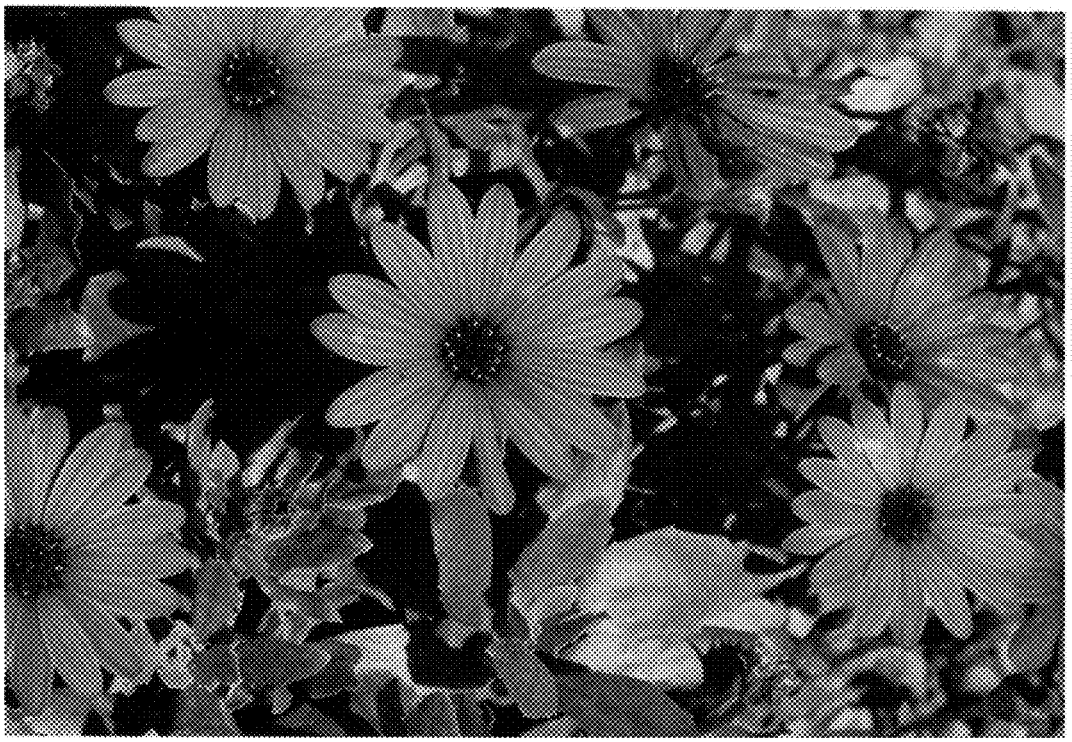

* * * * *